(12) United States Patent
Berland et al.

(10) Patent No.: US 10,405,787 B2
(45) Date of Patent: Sep. 10, 2019

(54) METHOD FOR MONITORING EXCREMENT DATA

(71) Applicant: SCA Hygiene Products AB, Göteborg (SE)

(72) Inventors: Carolyn Berland, Mölndal (SE); Mattias Bosaeus, Kallered (SE); Pär Johannesson, Västra Frölunda (SE)

(73) Assignee: ESSITY HYGIENE AND HEALTH AKTIEBOLAG, Göteborg (SE)

(*) Notice: Subject to any disclaimer, the term of this patent is extended or adjusted under 35 U.S.C. 154(b) by 257 days.

(21) Appl. No.: 15/104,261

(22) PCT Filed: Dec. 20, 2013

(86) PCT No.: PCT/SE2013/051598
§ 371 (c)(1),
(2) Date: Jun. 14, 2016

(87) PCT Pub. No.: WO2015/094065
PCT Pub. Date: Jun. 25, 2015

(65) Prior Publication Data
US 2016/0374607 A1   Dec. 29, 2016

(51) Int. Cl.
*G01N 33/48* (2006.01)
*A61B 5/20* (2006.01)
(Continued)

(52) U.S. Cl.
CPC ............ *A61B 5/202* (2013.01); *A61B 5/6808* (2013.01); *A61B 5/7235* (2013.01);
(Continued)

(58) Field of Classification Search
None
See application file for complete search history.

(56) References Cited

U.S. PATENT DOCUMENTS 5,258,745 A   11/1993   Colling
5,416,469 A    5/1995   Colling
(Continued)

FOREIGN PATENT DOCUMENTS

CA      2 859 144 A1    6/2013
WO   WO-96/14813 A1    5/1996
(Continued)

OTHER PUBLICATIONS

U.S. Appl. No. 15/104,296, filed Jun. 14, 2016, Carolyn Berland et al.
(Continued)

*Primary Examiner* — Larry D Riggs, II
(74) *Attorney, Agent, or Firm* — Drinker Biddle & Reath LLP

(57) ABSTRACT

A method, data processing unit, and system for monitoring excrement data for seeking a pattern for a monitoring period, wherein said excrement data is associated with at least one absorbent article and a person wearing said at least one absorbent article is disclosed. The method includes acquiring excrement data including excrement data for at least two different time periods, each substantially corresponding to the monitoring period for which a pattern of events is sought, wherein said excrement data includes information of excrement into an absorbent article in form of excrement events, and wherein each excrement event has an associated time mark or associated information from which an associated time mark may be derived; and smoothing the time mark of each excrement event.

18 Claims, 9 Drawing Sheets

(51) Int. Cl.
*A61F 13/42* (2006.01)
*A61B 5/00* (2006.01)
*G16H 50/20* (2018.01)
*G16H 50/30* (2018.01)

(52) U.S. Cl.
CPC .......... *A61B 5/7275* (2013.01); *A61B 5/7282* (2013.01); *A61F 13/42* (2013.01); *G16H 50/20* (2018.01); *A61B 5/6887* (2013.01); *G16H 50/30* (2018.01)

(56) References Cited

U.S. PATENT DOCUMENTS

| | | | |
|---|---|---|---|
| 7,250,547 | B1 | 7/2007 | Hofmeister et al. |
| 7,977,529 | B2 | 7/2011 | Bergman et al. |
| 2005/0156744 | A1 | 7/2005 | Pires |
| 2008/0214949 | A1 | 9/2008 | Stivoric et al. |
| 2008/0243099 | A1 | 10/2008 | Tippey et al. |
| 2008/0300651 | A1 | 12/2008 | Gerber et al. |
| 2011/0124982 | A1 | 5/2011 | Pipke |
| 2011/0263952 | A1 | 10/2011 | Bergman et al. |
| 2011/0295619 | A1 | 12/2011 | Tough |
| 2012/0173468 | A1 | 7/2012 | Gillam et al. |
| 2012/0220969 | A1 | 8/2012 | Jang et al. |
| 2012/0268278 | A1 | 10/2012 | Lewis et al. |
| 2013/0041334 | A1 | 2/2013 | Prioleau et al. |
| 2013/0137945 | A1 | 5/2013 | Addison et al. |
| 2013/0254141 | A1 | 9/2013 | Barda et al. |
| 2016/0314263 | A1 | 10/2016 | Berland et al. |
| 2016/0314264 | A1 | 10/2016 | Berland et al. |

FOREIGN PATENT DOCUMENTS

| | | |
|---|---|---|
| WO | WO-00/00144 A2 | 1/2000 |
| WO | WO-2004/100763 A2 | 11/2004 |
| WO | WO-2006/047815 A1 | 5/2006 |
| WO | WO-2011/054045 A1 | 5/2011 |
| WO | WO-2011/156862 A1 | 12/2011 |
| WO | WO-2013/003905 A1 | 1/2013 |
| WO | WO-2013/091728 A1 | 6/2013 |
| WO | WO-2013/095231 A1 | 6/2013 |

OTHER PUBLICATIONS

U.S. Appl. No. 15/104,320, filed Jun. 14, 2016, Carolyn Berland et al.
Australian examination report No. 2 dated Oct. 10, 2017 issued in related Australian patent application No. 201408431 (6 pages).
Extended European search report dated Apr. 18, 2017 issued in related European patent application No. 13899701.0 (8 pages).
Extended European search report dated Apr. 18, 2017 issued in related European patent application No. 13899366.2 (8 pages).
Office Action dated Mar. 21, 2018 issued in related European patent application No. 13 899 701.
Extended European search report dated Jul. 13, 2017 issued in corresponding European patent application No. 13 899 617.8 (7 pages).
Girish Keshav Palshikar: "Simple Algorithms for Peak Detection in Time-Series," ResearchGate, Jan. 1, 2009 (Jan. 1, 2009), pp. 1-13, XP055388742, Retrieved from the Internet: URL:https://www.researchgate.net/profile/Girish_Palshikar/publication/228853276_Simple_Algorit hms_for_Peak_Detection_in_Time-Series/links/53fd70ca0cf2364ccc08c4d8/Simple-Algorithms-for-Peak-Detection-in-Time-Series.pdf [retrieved on Jul. 6, 2017].

METHOD FOR MONITORING EXCREMENT DATA

CROSS-REFERENCE TO PRIOR APPLICATION

This application is a § 371 National Stage Application of PCT International Application No. PCT/SE2013051598 filed Dec. 20, 2013, which is incorporated herein in its entirety.

TECHNICAL FIELD

Generally, the disclosure relates to method for evaluating excrement data. The excrement data is associated with at least one absorbent article and a person wearing said at least one absorbent article. Further, the disclosure relates to a processing unit and system adapted to perform the method for evaluating excrement data.

TECHNICAL BACKGROUND

Systems for monitoring incontinence are known in the art. For instance, WO96/14813 A1 discloses an incontinence monitoring system and is particularly concerned with a system for the detection monitoring and management of urinary, faecal and other forms of incontinence. The system includes a plurality of sensors and a monitor to receive and record signals from the sensors, each sensor being adapted to be associated with a respective person and being responsive to urinary and/or faecal incontinence in that person. The monitor is capable of recording the time of onset of each incontinence condition and of indicating any regularity or pattern of incontinence in each said person. Over a period of time, for example 1 or 2 weeks, any pattern or regularity of incontinence periods for a particular patient may be identified from the recorded information, either manually or using appropriate software, and the patient, or nursing staff, may be arranged to anticipate an oncoming period of incontinence.

However, a drawback of the system disclosed in WO96/14813 A1 may be that the information recorded by the system may be difficult to interpret for identifying a pattern or regularity of incontinence periods for a particular patient. If the pattern or regularity is identified manually, the skills of the person identifying the pattern may affect the result. Further, such manual identification gives an arbitrary result. Still further, interpretation of complex data may be time consuming and the time available for the interpretation may affect the result.

Therefore, there is a need of improved methods and systems that at least alleviates the problems of prior art systems and offers identification of regularities or patterns from the recorded data such that the risk of misinterpretation as well as time consumed for analysis of the collected data is reduced. Further, there is a need of improved methods and systems for identifying such liquid discharge event patterns, which eliminates the dependency of the analysis result of knowledge of a person analysing recorded data as well as time available for analysis of recorded data.

SUMMARY

It is desired to obviate or at least alleviate the above mentioned problem. In a first aspect, the method for monitoring or evaluating excrement data, or excrement data, for seeking a pattern for a monitoring period includes, providing or acquiring excrement data including excrement data for at least two different time periods, each substantially corresponding to the monitoring period for which a pattern of events is sought; and smoothing the time mark of each excrement event. The excrement data is associated with at least one absorbent article and a person wearing said at least one absorbent article and includes information of excrement into an absorbent article in form of excrement events, and wherein each excrement event has an associated time mark or associated information from which an associated time mark may be derived.

Herein, absorbent article refers to an adult incontinence product, a baby or toddler diapers, sanitary towels, liners or other known absorbent articles.

The monitoring period, for which a pattern of events is sought, may be any period for which an event pattern is sought, for instance a 24 hour day, a period during which the person wearing said at least one absorbent article is awake, a shift etc. The time periods for which data is provided or acquired form together a measurement period, which might be continuous or discontinuous. The different time periods may originate from any different/separate days or shifts, such as subsequent days or days with one or several days in between as far as the incontinence condition of the person wearing the absorbent article is not significantly changed. In all examples above, the time periods of data that corresponds to the monitoring period is intended to mean that the period corresponds to approximately same hours (or minutes) of day.

The excrement data may include information of excrement events in from of vector including merely time marks for each detected or occurred event, in form of a matrix including both time marks in one column and some kind of indication for each detected event in another column, such as symbols or numbers 0 (for non-events) and 1 (indicating events), respectively. The time marks may include information in form of minutes, in form of hours and minutes irrespective of the day, or in form of days, hours, and minutes.

The excrement may be in form of faeces, urine, or a mixture thereof.

According to an exemplary embodiment, the method may further include combining the excrement data of the at least two different time periods to aggregated data extending over the monitoring period, covering the data for the at least two different time periods.

According to an exemplary embodiment, combining the data to excrement data of the at least two different time periods to aggregated data may include superposing the excrement data of the at least two different time periods such that each event of the superposed excrement data is distinguishable.

According to an exemplary embodiment, the excrement data may be in form of absorbent state data and an excrement event is indicated by a change of the absorbent state of the absorbent article.

An absorbent state, as used herein, is intended to mean any state indicative of the amount absorbed by the absorbent article. Thus, also an absorbent article which has not yet absorbed any supplies of excrement is considered to have an absorbent state. A change in an absorbent state of an absorbent article, as used herein, is intended to mean any change of the absorbent state, from a first substantially stable absorbent state to any other substantially stable absorbent state. As used herein, a stable state is intended to mean a state which is substantially constant during a period of time, such as at least a period having the length of an interval into which the monitoring period is divided. A change of absorbent state may occur due to excrement into the absorbent article, that is, an excrement event. A change from an absorbent state being indicative of a dry article into an absorbent state being indicative of an article which has received a supply if excrement is also considered to be a change of absorbent state.

According to an exemplary embodiment, the excrement data may be in form of electrical property data and an excrement event is indicated by a change of the electrical property of the absorbent article.

According to an exemplary embodiment, the excrement data may be in form of absorbed volume data and an excrement event is indicated by a change of the absorbed volume of the absorbent article.

According to an exemplary embodiment, smoothing may include smoothing by applying a Kernel smoothing method.

According to an exemplary embodiment, the Kernel smoothing method may include by applying a Kernel function to the time mark of each excrement event.

According to an exemplary embodiment, the Kernel function may be a scaled Kernel function.

According to an exemplary embodiment, a bandwidth, h, of said Kernel function may be 20-150 minutes, may be 30-90 minutes, may be 45-75 minutes, or may be 55-65 minutes.

According to an exemplary embodiment, a bandwidth, h, of said Kernel smoothing may be approximately 1 hour.

According to an exemplary embodiment, a bandwidth, h, of said Kernel smoothing may be the standard deviation of the Kernel function.

According to an exemplary embodiment, the Kernel function may be symmetric in relation to the time mark, the Kernel smoothing function may be in form of a uniform, a triangular, or a Gaussian function.

If the Kernel function is in form of a Gaussian function, the bandwidth will be the standard deviation of the Gaussian function.

According to an exemplary embodiment, the aggregated data may be in form of a continuous function including superposed Kernel functions associated with each time mark of each excrement event.

According to an exemplary embodiment, a pattern of excrement events for the person associated with the absorbent article may be estimated based on the aggregated data including smoothed time marks for each excrement event.

According to an exemplary embodiment, the method may further include identifying each peak of the aggregated data having a height$\geq 0.8*n*k$, a height$\geq 0.9*n*k$, or a height$\geq 0.95*n*k$, wherein n is number of different periods for which data is acquired corresponding to the monitoring period and k is the height of the smoothing function.

That is, the peaks having a height equal to or higher than $0.8*n*k$, having a height equal to or higher than $0.9\ n*k$, or having a height equal to or higher than $0.95*n*k$, wherein n is number of different periods for which data is acquired corresponding to the monitoring period and k is the height of the smoothing function, may be identified.

Generally, peaks having such height are an indication of a recurring excrement event. That is, an excrement event has occurred, or is considered to have occurred, at the peaks having such height during all the different time periods, corresponding to the monitoring period, for which data is acquired or provided.

According to an exemplary embodiment, the method may further include estimating each time mark corresponding to each identified peak.

According to an exemplary embodiment, the method may further include recording each estimated time mark.

According to an exemplary embodiment, the method may further include recommending toileting during a time interval prior to each of the estimated time marks corresponding to each identified peak, wherein said time interval has a length corresponding to the bandwidth.

According to an exemplary embodiment, the method may further include associating each time mark of each identified peak to a corresponding time interval having a length corresponding to the bandwidth h, and thereafter recommending toileting during a time interval, having a length corresponding to the bandwidth h, prior to each time interval associated with the time mark of each peak.

According to an exemplary embodiment, the excrement data may be collected or acquired using said sensor associated with the absorbent article, for example said at least one absorbent article includes said sensor.

The sensor may be any suitable sensor, such as a liquid discharge sensor, a gas sensor, a temperature sensor, as long as the sensor is able to detect excrement supply into an absorbent article.

According to an exemplary embodiment, the total number of periods of time for which data may be acquired or provided, corresponding to the monitoring period, may be pre-determined, may correspond to 2 to 5 monitoring periods, may be at least approximately 3 monitoring periods, or may substantially correspond to 3 monitoring periods.

Thus, for a monitoring period of 24 hours this corresponds to time periods having together the length of 48 to 120 hours, or at least approximately 72 hours. In situations where there are possible errors in the equipment or the care takers or patients are not behaving as expected during the time periods, for instance due to the condition of the care taker, acquiring data for longer periods may be advantageous, such as 4 days. In such a case, the data might be discontinuous. It is advantageous if the acquired data for all periods together covers substantially at least three monitoring periods.

According to an exemplary embodiment, the method may further include plotting the resulting superposed data as a continuous curve over the monitoring period for visualising a pattern of excrement events based on the acquired or provided data.

According to an exemplary embodiment, the method may further include identifying all peaks of the superposed data and the corresponding time marks.

As used herein, peaks means generally all peaks, not only the peaks having a height equal to or higher than $0.8*n$ times k, where n is the number of periods for which data is acquired or provided and k is the height of the smoothing function. Identifying or estimating the peaks is advantageous, since that makes it possible to estimate the number of excrement events from the height of each peak for each corresponding time mark.

According to an exemplary embodiment, the height of each of the detected peaks may be divided by the height of the smoothing function applied to each time mark, for finding number of excrement events corresponding to each corresponding time mark.

According to an exemplary embodiment, the method may further include providing a series of time intervals extending together over the monitoring period, and associating each time mark associated with a peak with the corresponding time interval and associating the number of excrement events corresponding to the peak with the corresponding time interval.

According to an exemplary embodiment, the number of associated excrement events for each time interval may be arranged in form of a histogram.

According to an exemplary embodiment, the number of associated excrement events for each time interval may be arranged in form of a circumferential diagram extending over the monitoring period, wherein each segment of the diagram corresponds to each of the time intervals.

As used herein, a circumferential diagram or time diagram is intended to mean a diagram which has a circumferential form, wherein the start time and end time coincide, such as a circular diagram, a 24 hour clock diagram, a quadratic 24 hour clock diagram or any other circumferential form suitable for illustrating the information.

According to an exemplary embodiment, each segment of the circumferential diagram may correspond to 55 to 65 minutes.

According to an exemplary embodiment, the number of associated excrement events for each time interval may be associated with a graphical scheme which is applied to the segments of said circumferential diagram.

The graphical scheme may be in form of a colour or shade gradient or different density for one colour, or different colours for different number of events, or any other suitable graphical scheme etc.

According to an exemplary embodiment, the graphical scheme may be in form of a colour gradient, for example associating an increasing darkness with an increasing number of associated excrement events.

A second aspect relates to a data processing unit for monitoring or evaluating excrement data. The data processing unit is adapted to process an output signal generated by a sensor associated with an absorbent article. The data processing unit is configured or adapted to acquire excrement data or excrement data; and smoothing the time mark of each excrement event. The excrement data includes data for at least two different time periods, each substantially corresponding to the monitoring period for which a pattern of events is sought and information of excrement into an absorbent article in form of excrement events, and wherein each excrement event has associated information from which an associated time mark may be derived.

According to an exemplary embodiment, the data processing unit may be adapted to perform a method according to the first aspect.

A third aspect relates to a system for monitoring or evaluating excrement data. The system includes a sensor associated with an absorbent article, and a data processing unit adapted to process said output signal generated by the sensor. The sensor is arranged to generate an output signal representative of the excrement state of said absorbent article. The data processing unit is adapted to acquire excrement data including excrement data for at least two different time periods, each substantially corresponding to the monitoring period for which a pattern of events is sought, wherein said excrement data includes information of excrement into an absorbent article in form of excrement events, and wherein each excrement event has associated information from which an associated time mark may be derived; and smoothing the time mark of each excrement event.

As used herein, excrement state is intended to mean a state or property of the absorbent article indicative of occurred excrement events, if any.

According to an exemplary embodiment, the data processing unit may be a data processing unit according to the second aspect. Thus, the data processing unit is adapted to perform or execute the method according to first aspect.

According to an exemplary embodiment, the system may further include output means for visually representing the aggregated excrement data for visualising a pattern of excrement events for the person associated with the absorbent article, based on the acquired or provided excrement data.

Generally, all terms used in the claims are to be interpreted according to their ordinary meaning in the technical field, unless explicitly defined otherwise herein. All references to "a/an/the element, device, component, means, step, etc" are to be interpreted openly as referring to at least one instance of said element, device, component, means, step, etc., unless explicitly stated otherwise.

Other objectives, features and advantages of the present invention will appear from the following detailed disclosure, from the attached claims as well as from the drawings.

BRIEF DESCRIPTION OF THE DRAWINGS

These and other aspects of the present disclosure will now be described in more detail, with reference to the appended drawings showing embodiment(s) thereof, in which.

All the figures are highly schematic, not necessarily to scale, and they show only parts which are necessary in order to elucidate the disclosure, other parts being omitted or merely suggested.

DETAILED DESCRIPTION OF PARTICULAR EMBODIMENTS

The invention will now, by way of example, be described in more detail by means of embodiments and with reference to the accompanying drawings, but should not be limited thereto.

Figure 1:
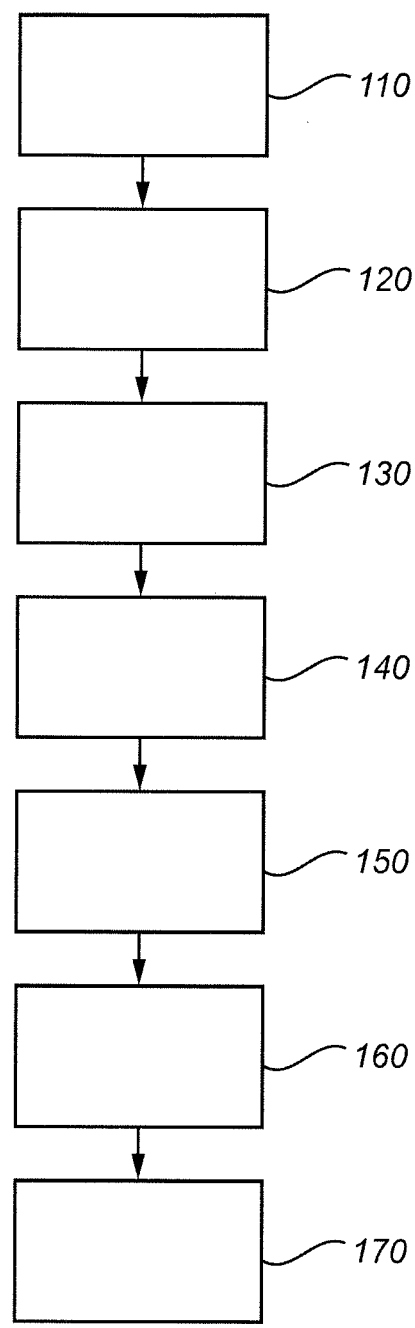
FIG. 1 is a flow chart illustrating schematically a method for monitoring excrement data according to at least an exemplary embodiment of one aspect of the present disclosure.

FIG. 1 illustrates a method for monitoring or evaluating excrement data, or excrement data, for seeking a pattern for a monitoring period by a flow chart. The excrement data is associated both with at least one absorbent article and with a person wearing said at least one absorbent article. The method includes:

acquiring excrement data including excrement data 110 for at least two different time periods, each substantially corresponding to the monitoring period for which a pattern of events is sought, wherein said excrement data includes information of excrement into an absorbent article in form of excrement events, and wherein each excrement event has an associated time mark or associated time information from which an associated time mark may be derived;

providing a series of sequential non-overlapping time intervals 120, together extending substantially over the monitoring period; and associating the time mark associated with each excrement event with a corresponding time interval 130.

By providing a series of sequential non-overlapping time intervals, together extending substantially over the monitoring period the monitoring period may be divided into a series of time intervals. Therefore, the length of said time intervals is shorter than said period of time for which data is provided and a sum of the length of said time intervals substantially equals the length of the monitoring period. The monitoring period, for which a pattern of events is sought, may be any period for which an event pattern is sought, for instance a 24 hour day, a period during which the person wearing said at least one absorbent article is awake, a shift at a nursing home, etc. The excrement data may be provided for a monitoring period which is continuous or discontinuous. The different time periods may originate from any different/separate days or shifts, such as subsequent days or days with one or several days in between as far as the incontinence condition of the person wearing the absorbent article is not significantly changed. For all examples above, the time periods of data that corresponds to the monitoring period is intended to mean that the period corresponds substantially to same hours (or minutes) of day.

The excrement data includes information of excrement events in form of a vector or matrix including merely time marks for each detected or occurred event. The time marks includes information for the actual times when an excrement event has occurred, is detected, or is considered to have occurred in form of days, hours, and minutes. The method may be applied to excrement data of different types. For instance, the time marks of the excrement data may be alternatively arranged as a matrix including day or date in one column, hour in another column and minutes in a third column, which are associated with each other. The data in form of days, hours and minutes, may be arranged to subgroups irrespective of the day. By disregarding the day the data is superposed without losing any information of each separate excrement event.

Figure 2:
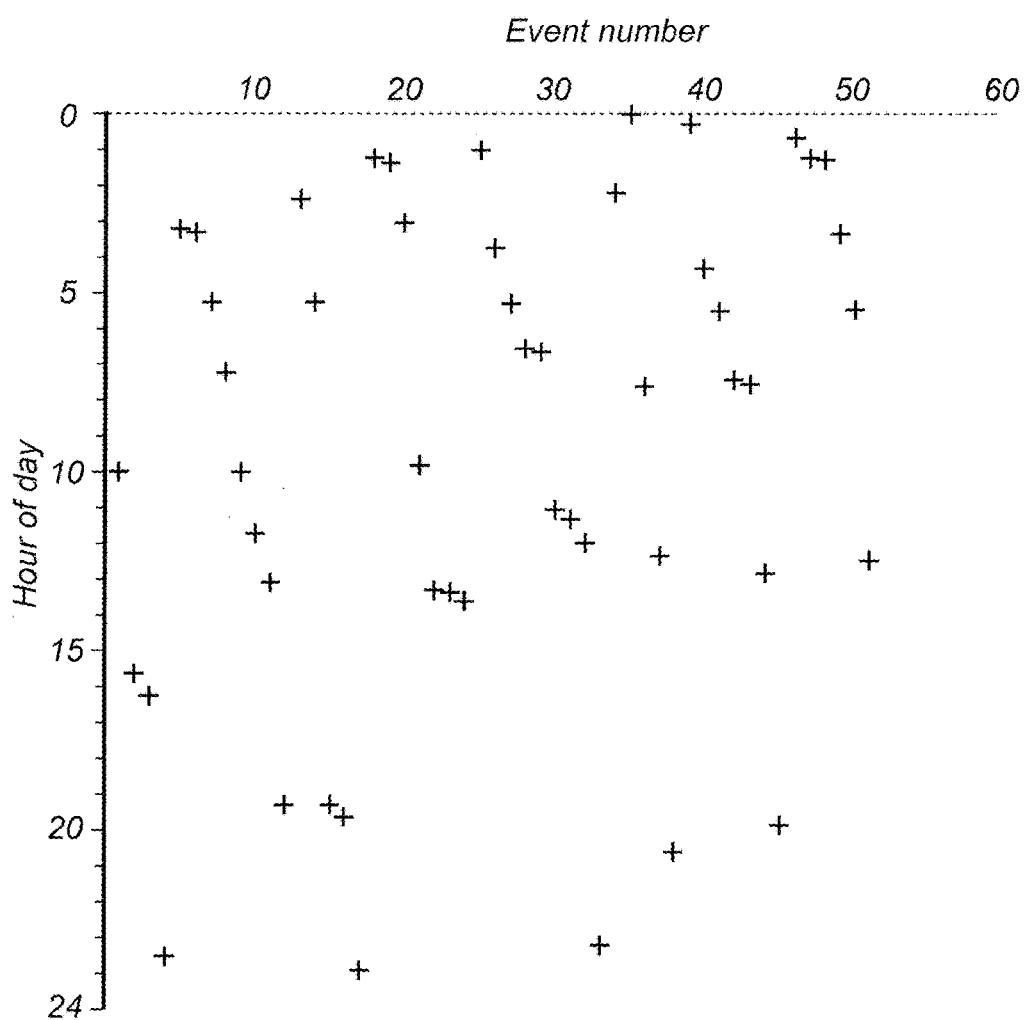
FIG. 2 is an example of excrement data acquired for an absorbent article during a period of 7 days.

FIG. 2 shows excrement data acquired for a total measurement period of seven days, including data for seven different time periods, corresponding to the at least two time periods of the claims, and for a monitoring period of a 24 hour day. The time in hours is on y axis and the number of void is in chronological order on x axis. The excrement data or the excrement data of the seven different periods of time is combined to aggregated data extending over the 24 hour monitoring period. The aggregated data in FIG. 2 covers the data for the seven different time periods for which data is provided. The excrement data of the seven different time periods is aggregated by superposing the data of the different periods. The data of the different periods is superposed such that each event of the superposed excrement data for the seven different time periods is distinguishable. Also, the hours of each of the seven different time periods, which are superposed, coincide with the hours of the monitoring period.

In FIG. 2, the aggregated or superposed excrement data is plotted at the actual time of the events, that is, not associated or correlated with an interval into which the monitoring period (in this case a 24 hour day) is divided. It is clear from FIG. 2 that a pattern of events is relatively difficult to identify quickly based on a graph of unanalysed data.

Alternatively, each time mark may include information for the actual times when an excrement event has occurred, is detected, or is considered to have occurred in form of minutes irrespective of the day. In such a case, each time mark for the first time period of the at least two different periods, or the first day, includes the time between the beginning of the total period and the point of time each excrement event is considered to have occurred, or is detected, in minutes. For the second time period each time mark in such a case includes the length of the first time period in minutes and the time between the beginning of the second period and the point of time each the excrement event is considered to have occurred, or is detected, in minutes, that is, the number of minutes from the beginning of the second period until each excrement event is considered to have occurred or is detected. From this type of data, time marks for excrement events of each time period may be obtained by subtracting the length of each time period in minutes from each time mark originating from each subsequent time period after the first, i.e. the second, third, etc. in this way the data for each different period may be superposed or added together without losing any information of occurred or detected excrement events. Thereafter, the time marks of the excrement events may be associated with the time intervals into which each monitoring period is divided into.

Still alternatively, the time marks may include information in form of hours and minutes irrespective of the day. In such a case the time marks are similar to those as described for minutes above, but in form of hours and minutes. Thereafter, the data is handled similarly as is described above.

The excrement data may include information of excrement events in any suitable form, such as raw data for change in electrical property, in form of a vector including merely time marks for each detected or occurred change. Alternatively, excrement data may include information in form of a matrix including both time marks in one column and some kind of indication for each detected change, i.e. event, in another column, such as symbols or numbers 0 (for non-changes) and 1 (indicating changes), respectively. The time marks may include information in form of minutes, in form of hours and minutes irrespective of the day, or in form of days, hours, and minutes.

The association of time interval may mean association in form of correlation to a time interval which is relatively shorter than the monitoring period, or association with a bandwidth of a Kernel smoothing applied to the time marks, or any other similar association with a time period.

The excrement may be in form of faeces, urine, or a mixture thereof. The data may include data for both supply of faeces events and supply of urine events, which events might be discriminated from each other, if desired, a combination of such events, or only one type of events. Data for different types of events may be analysed together or separately.

In the embodiment in FIG. 1, the excrement events are detected based on data acquired by a sensor associated with the absorbent article prior to associating/correlating each time mark of each excrement event with a corresponding time interval. The excrement events may be automatically detected by the system. The sensor may be any suitable sensor, such as a liquid discharge sensor, a gas sensor, a temperature sensor, as long as the sensor is adapted to detect supply of excrement into the absorbent article.

Figure 4:
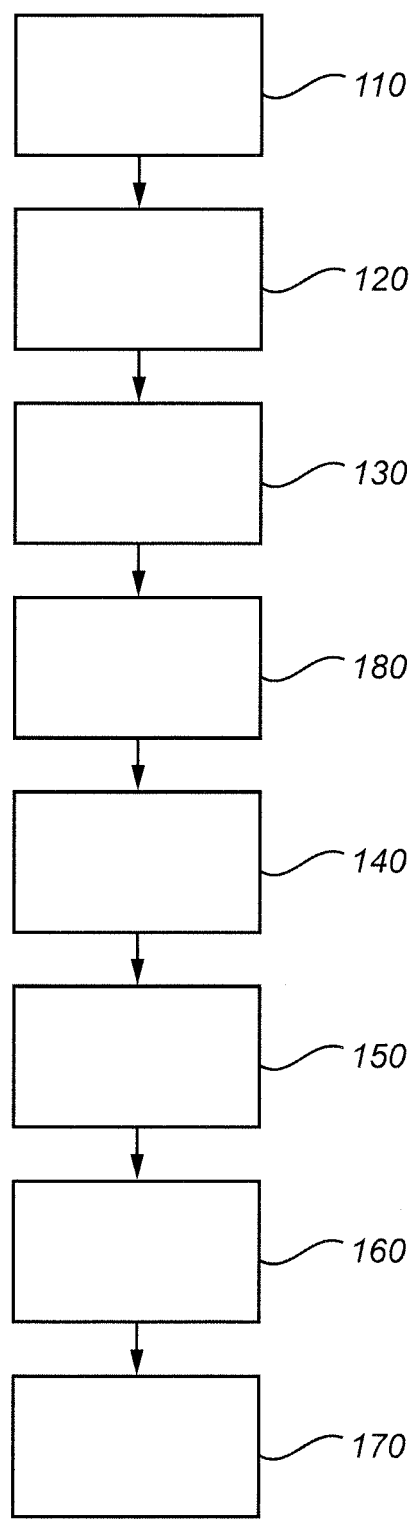
FIG. 4 is a flow chart illustrating schematically a method for monitoring excrement data according to at least an exemplary embodiment of one aspect of the present disclosure.

In the exemplary embodiment in FIG. 4, associating the time mark associated with each excrement event with the corresponding time interval is in form of correlating 130' the time mark of each excrement event with the corresponding time interval independently of the time period to which said excrement event corresponds/is associated with.

The method illustrated in FIG. 4, further includes arranging the excrement data into subsets 140 based on the correlation of each time mark with the corresponding time interval of said first series of intervals over time. Such arrangement results in subsets of data in form of combined data for all different time periods. In other words, arranging the data into subsets 140 is a way of combining data to subsets of data corresponding to each time interval. A number of events for each time interval may be obtained by calculating the number of events corresponding to each subset. In this way a pattern over a number of time periods, such as days, corresponding to the monitoring period may be obtained. From such a pattern time intervals for recurring excrement events may be obtained.

The data arranged to subsets is associated or correlated with a corresponding time interval of the provided series of sequential non-overlapping time intervals, which dived the monitoring period into intervals. Alternatively, the aggregated or superposed data may be arranged associated or correlated with a corresponding time interval of the provided series of sequential non-overlapping time intervals, together covering the monitoring period, such that the monitoring period is divided into intervals.

Figure 3:
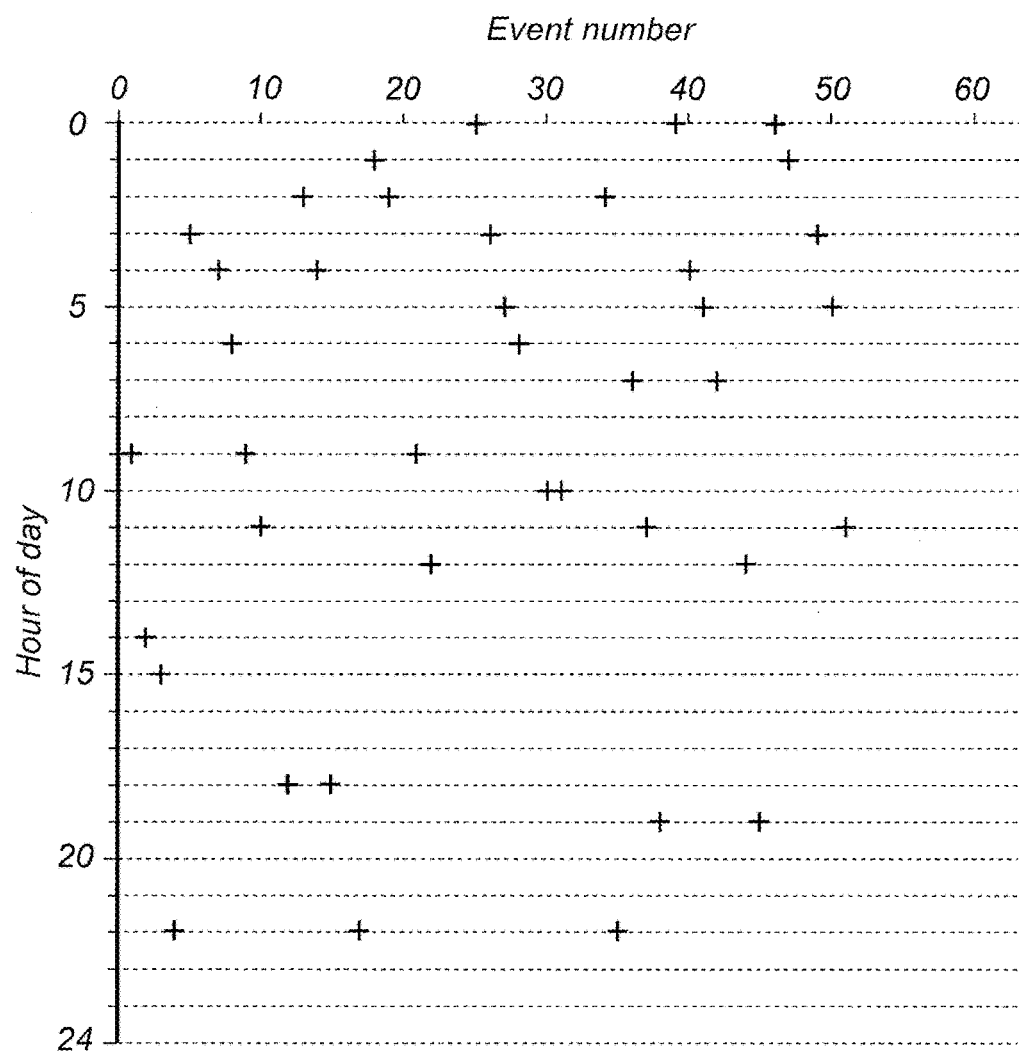
FIG. 3 is an example of excrement data acquired for an absorbent article during a period of 7 days evaluated according to an exemplary embodiment of the disclosure.

FIG. 3 shows excrement data for three different time periods, here three days, for which data is provided, and for a monitoring period of one 24 hour day. In FIG. 3, the excrement data or the excrement data of the three different periods of time is combined to aggregated data extending over the 24 hour monitoring period. The aggregated data in FIG. 3 cover the data for the three different time periods for which data is provided. The excrement data of the three different time periods is aggregated by superposing the data of the different periods. The data of the different periods is superposed such that each event of the aggregated excrement data for the three different time periods is distinguishable. Also, the hours of each of the three different time periods, which are superposed, coincide with the hours or minutes of the monitoring period.

In FIG. 3 time in hours is on y axis and the event number on x axis. The events are numbered in chronological order and the first event is assigned number 1. For the embodiment in FIG. 3, the non-overlapping sequential time intervals have a length of 1 hour and extend between: 00 and 01, 01 and 02, 02 and 03, 03 and 04 etc. Thus, in FIG. 3 the data is associated or correlated to time intervals having a length of one hour. Thereafter, the data is plotted independently of the exact time mark of each excrement event. Instead, the correlated or associated time intervals are used. Thus, the events having a time mark between 00 and 01 is plotted at 00, the events having a time mark between 01 and 02 is plotted at 01, the events having a time mark between 02 and 03 is plotted at 02, etc. Alternatively, the time marks of the events may be plotted somewhere between the end points of each of the time intervals, or at the other end point of each time interval. The number of excrement events for each time interval may be determined. For instance, for excrement data shown in FIG. 3, the number of time events associated with the time interval between 11 and 12 is 3.

Alternatively, the data may first be associated with the time intervals into which together extend over the monitoring period, or into which the monitoring period is divided, and thereafter the data relating to different measurement periods may be superposed.

The method further includes calculating the number of events 150 associated or correlated with each time interval and estimating a pattern 160 of excrement events for the person associated with the absorbent article is estimated based on the calculation of the number of events associated or correlated with each time interval.

According to the exemplary embodiment in FIG. 1, the number of events associated or correlated with a time interval, which is equal to or larger than the number of different time periods, corresponding to the monitoring period, for which data is provided is indicative of a recurring excrement event. The method in FIG. 1 further includes (automatically) recommending toileting 170 of the person associated with the data during the time interval prior to a time interval which is associated with a number of events which is equal to or larger than the number of different time periods, corresponding to the monitoring period, for which data is provided. Such a recommendation provides the care giver automatically a toileting interval during which it is advantageous to take the person associated with the absorbent article, i.e. the care taker to the toilet. A recommended time interval for toileting is more advantageous than a recommended specific time, since it makes it easier for the care giver to plan their work. The recommendation may be in form of a printed list of recommended toileting time intervals or in form of a diagram with graphical indications for recommended toileting intervals.

In the embodiment in FIG. 1, the series of sequential time intervals are non-selectable by a user and/or the time intervals have non-selectable lengths. Further, the lengths of the time intervals can be equal. That is, a person using the system, i.e. an operator or a nurse, cannot select the length of the time intervals. The predetermined series of time intervals are predetermined in respect of the number of time intervals, the length of the time intervals, the sum of the length of the time intervals, and/or the alignment of the time intervals in relation to the monitoring period, etc. According to an alternative embodiment, the series of sequential time intervals are determined or preselected by the method or by the system adapted to perform the method.

The length of each of said predetermined time intervals is 20 minutes to 150 minutes, 30 to 90 minutes, 45 to 75 minutes, or 55 to 65 minutes. The total period of time for which data is provided, including the at least two different time periods of the claims, is predetermined, and, in particular embodiments, a length of two to fourteen times the length of the monitoring period for which a pattern of events is sought, a length of at least three times the length of the monitoring period, or substantially a length of three times the length of the monitoring period. That is, for being able to ensure that the found patter of events is reliable, the excrement data includes data for at least a total period covering two to fourteen different periods corresponding to the monitoring period. Especially, the inventors have found that data for a total period covering three different time periods is a good compromise between the reliability of the estimated pattern and need and cost for measurements. The total period of time for which data is provided may be continuous or discontinuous. If the total period is discontinuous, the length of the period for which data is provided is considered to be a sum of the partial periods, which are separated from each other by periods for which data is not provided.

Further, the absorbent article includes a sensor, and said excrement data is collected or acquired using the sensor. The sensor is described more in detail below when the system is described.

The method further includes smoothing each time mark of an excrement event 180. As a result of the smoothing each time mark may be considered to be associated with a probability in time during which the corresponding excrement event may occur. In the example in FIG. 4, smoothing is performed by applying a Kernel smoothing method, that is, a Kernel function is applied after associating each time mark with a corresponding time interval. However, if smoothing is performed, the time marks of the excrement events in the excrement data are smoothed. Alternatively, the smoothing may be performed before associating each time mark with a corresponding time interval.

During smoothing, each time mark of an excrement event in the excrement data is associated with a Kernel function. That is, a Kernel function is applied to each time mark of an excrement event in the excrement data. The Kernel function has a predetermined arbitrary height corresponding to a single excrement event and a suitable bandwidth, h, as defined by the standard deviation of the Kernel function is chosen. The Kernel function may be a scaled Kernel function.

Figure 5:
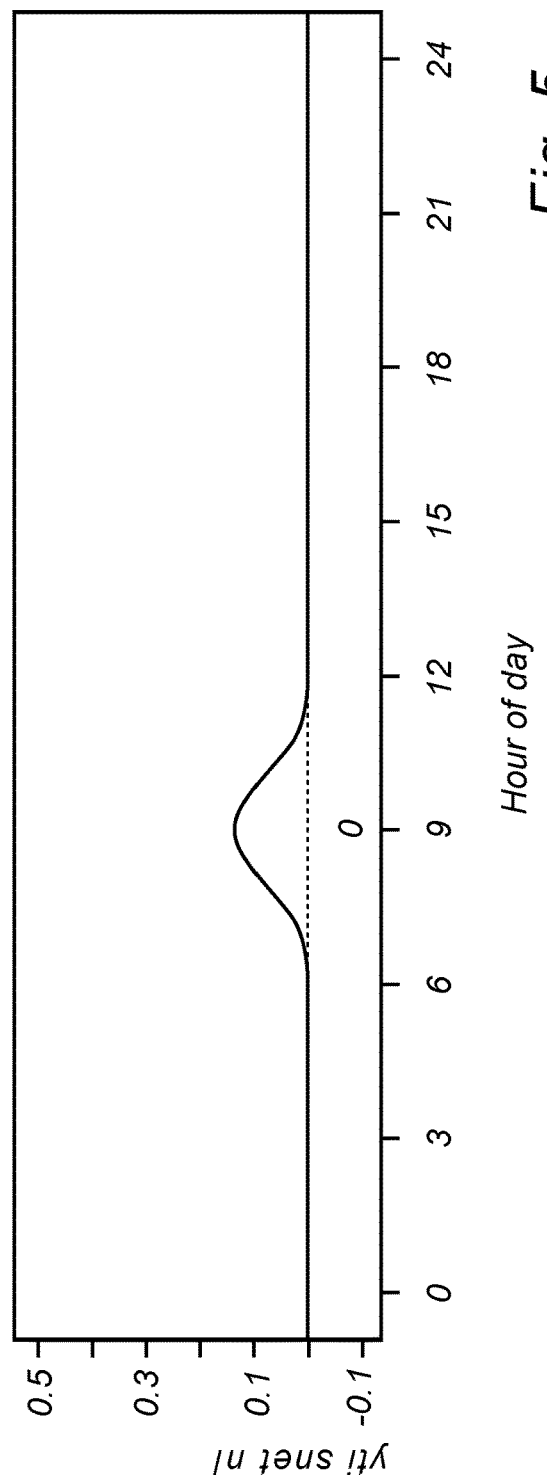
FIG. 5 is an example of a smoothing function according to an exemplary embodiment.

FIG. 5 shows a time mark for an excrement event at 9 am and a Kernel function applied to the event. As is obvious from FIG. 5, the Kernel function is symmetric around each time mark. That is, the time mark is at the centre of a symmetric function having equal extension in time before as well as after the time mark. The Kernel function in FIG. 5 is in form of a Gaussian function.

Generally, the Gaussian function, K, is expressed as:

$$K(t) = \frac{1}{\sqrt{2\pi}} e^{-\frac{1}{2}t^2}$$

A scaled Gaussian function, $K_h$, is expressed as:

$$K_h(t) = \frac{1}{\sqrt{2\pi h^2}} e^{-\frac{1}{2}\left(\frac{t}{h}\right)^2}$$

Where h, is the standard deviation, which is the bandwidth of the Kernel function.

By applying a symmetric Kernel function to each time mark of the excrement events, the time marks of each event is assigned an extension in time, instead of being a single point of time. The extension in time corresponds to time interval during which there is a probability that each supply of excrement might occur. That is, each excrement event may, likely, occur slightly before or slightly after the corresponding time mark. When a Gaussian Kernel function is applied, each excrement event occurs most likely at the centre of the Gaussian function, which equals to the time marks of the excrement events of the excrement data.

By smoothing the time marks of the excrement events, a time mark for an excrement event slightly after a specific time interval may be linked to a group of time marks associated with the specific time interval relatively simply and efficiently. Alternatively, an excrement event slightly before a specific time interval may be linked to a group of excrement events associated with the specific adjacent later time interval.

Figure 6:
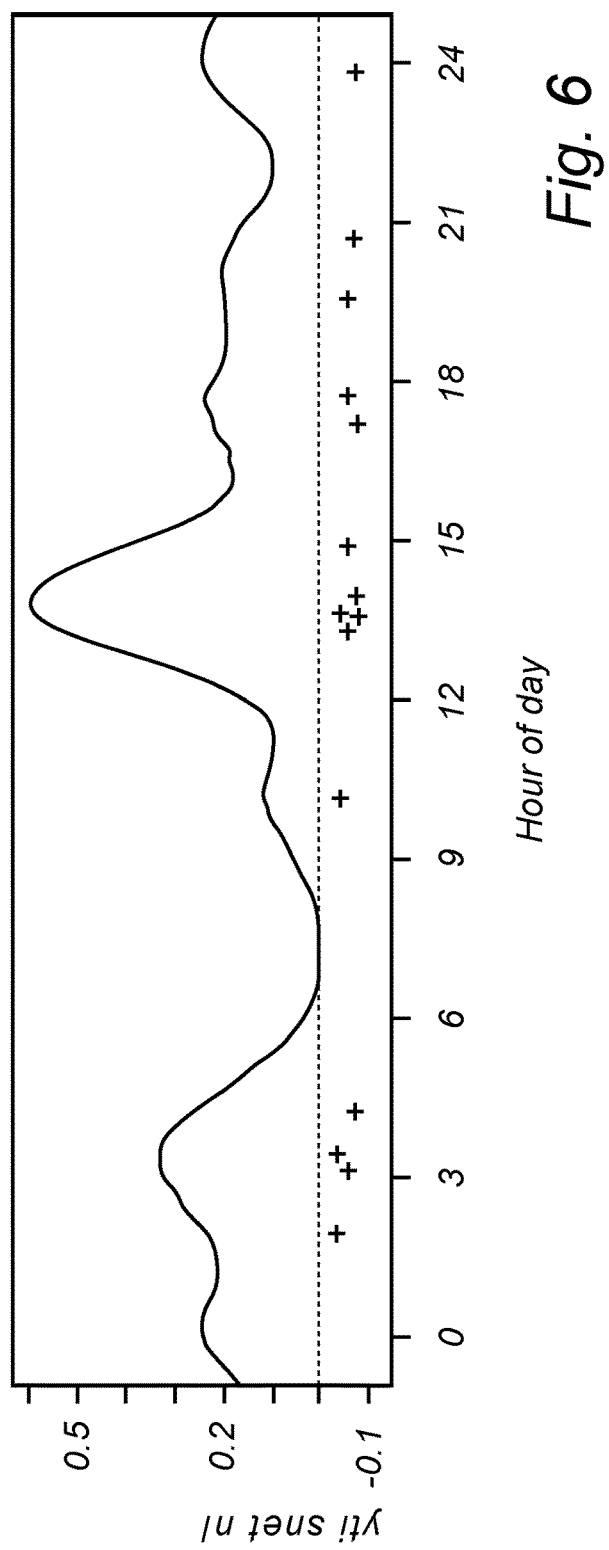
FIG. 6 is an example of excrement data monitored according to an exemplary embodiment of method of the present disclosure.

FIG. 6 discloses excrement data, or supply of excrement data, monitored according to at least an embodiment of the inventive method for a total measurement period or time period of three 24 hour days. For the excrement data in FIG. 6 the monitoring period is a 24 hour day. The excrement data is provided for a total time period of three 24 hour days, corresponding to three different time periods for which data is provided and which correspond to the 24 hour monitoring period. The excrement data of the three different periods of time is combined to aggregated data extending over the 24 hour monitoring period. The aggregated data in FIG. 6 cover the data for the three different time periods for which data is provided. The excrement data of the three different time periods is aggregated by superposing the data of the different periods. The data of the different periods is superposed such that the number of events for each of the three different time periods is distinguishable in the superposed excrement data. Also, the hours of each of the three different time periods of the excrement data, the data of which is superposed, coincide with the hours of the monitoring period.

The time marks of the excrement events of aggregated or superposed excrement data is plotted in the FIG. 6 as plus symbols below zero line. Thereafter, the time marks of each of the supply excrement events are smoothed by applying a Kernel function. In the example in FIG. 6 a kernel function in form of a Gaussian function having a height approximately 0.1 and a bandwidth of approximately 1 hour is applied to each time mark of the excrement data.

The resulting smoothed excrement data is plotted as a continuous curve in FIG. 6. From such a continuous curve the pattern of excrement events is visible in form of peaks. From such a continuous curve peaks having a value equal to or higher than n*k, where n is the number of time periods, corresponding to the monitoring period, for which data is provided, and k is the predetermined height of the kernel function applied to each time mark, may be identified. The peaks may be identified by estimating the time marks corresponding to a change from positive first derivative to negative first derivative of the continuous curve or by other methods known by the person skilled in the art. Since the excrement events are associated with or correlated to a corresponding time interval, the peaks may as well be associated with or correlated to a corresponding time interval. In addition to including information for all the excrement events associated with each time interval itself, if a series of time intervals together extending over the monitoring period would be provided, the peaks would include information for excrement events adjacent to each time interval. Depending on the chosen bandwidth the influence of excrement events within one time interval to adjacent another time interval may be influenced.

From FIG. 6, it is clear that using an embodiment of the inventive method, for instance, the four events having time marks around 13 and 14 may be linked to a single group, instead of one of them being a single event in another interval than the three others.

In FIG. 6, it is clear that a recurring excrement event is likely to occur between 13.00 and 14.00 or 1 pm and 2 pm. Also, there is a smaller peak around 03.00 or 3 am.

From such a continuous curve, especially peaks equal to or higher than the number of monitoring periods, n, for which data is provided times the predetermined height, k, for a single kernel function may be identified, i.e. peaks having approximately a height equal to or higher than k*n may be identified. The peaks may be identified by estimating the time marks corresponding to a change from positive first derivative to negative first derivative of the continuous curve or by other methods known by the person skilled in the art. Thereafter, the time mark of the peak may be associated to a time interval having same length as the bandwidth, and toileting may be recommended during a toileting time interval prior the time interval to which the time mark of the peak is associated. The toileting time interval has the same length as the bandwidth for the Kernel. For instance, in FIG. 6, if the time mark for the peak is ca. 13.30, this time mark may be associated to a time interval between 13.00 and 14.00, or 1 pm and 2 pm. Thus, toileting may be recommended during a toileting time interval extending between 12.00 and 13.00.

Alternatively, if a series of time intervals extending together over the monitoring period is provided, the peaks may be associated with or correlated to a corresponding time interval by identifying the corresponding time marks for each peak and by correlating or associating the identified time marks to a corresponding time interval.

Further, all peaks and their corresponding time marks may be identified and thereafter divided by k, the height of the Kernel function. Thus, the number of excrement events corresponding to the identified peaks and their time marks may be calculated. Such information may be visually represented. The peaks may be identified by estimating the time marks corresponding to a change from positive first derivative to negative first derivative of the continuous curve or by other methods known by the person skilled in the art.

Still alternatively, if the excrement events are associated with or correlated to a corresponding time interval prior to smoothing and the exact time marks are smoothed, such information may be used for identifying time intervals corresponding to the peaks.

The inventors have found that a suitable bandwidth h of the Kernel function is 20-150 minutes, 30-90 minutes, 45-75 minutes, or 55-65 minutes. Especially, the inventors have found that for evaluating excrement data, a bandwidth of 1 hour is advantageous.

Alternatively, the Kernel function may be another symmetric function having equal extension before and after the time mark, such as a uniform, a triangular, an Epanechikov, a quartic (biweight), a triweight, a tricube, or cosine function. The functions are well known for the skilled person and are therefore not explained in detail here.

In some cases, an asymmetric Kernel function may be advantageous. For instance, before bedtime a Kernel function having an extension in time before the time mark may be useful since in that way a wetness event occurring slightly after a time interval before bedtime may be associated to the time interval before bedtime instead of the time interval after bedtime.

Further, the method includes visually representing the number of associated excrement events for each time interval for visualising a pattern of excrement events based on the provided excrement data. The number of associated excrement events for each sequential time interval is arranged in form of a diagram or time diagram extending over the monitoring period, wherein each segment of the diagram or time diagram is corresponding to each time interval into which the monitoring period is divided and wherein the number of excrement events is associated with the corresponding segment. Especially, it is advantageous to associate the number of excrement events for the aggregated or superposed data associated with a time interval with a segment of a diagram or time diagram. The number of excrement events for the aggregated or superposed data may be calculated using the methods described above. As used herein, time diagram is intended to mean a diagram which has a linear or circumferential form, wherein each segment is associated with a specified time interval.

According to the method, calculating the number of excrement events corresponding to each time interval includes calculating a sum of excrement events originating from all periods for which data is provided, each of which periods corresponds to the monitoring period, and corresponding to each time interval. Suitably, the method includes correlating the time mark of each excrement event with a corresponding time interval prior to calculating the number of excrement events corresponding to each time interval. In the exemplary embodiment, the time intervals are predetermined, that is, the number of time intervals, the length of the time intervals, the sum of the length of the time intervals, and/or the alignment of the time series in relation to the monitoring period, etc. are predetermined. Further, predetermined series of time intervals are intended to be predetermined in respect of the number of time intervals, the length of the time intervals, the sum of the length of the time intervals, or the alignment of the time intervals in relation to the monitoring period, etc.

Figure 7:
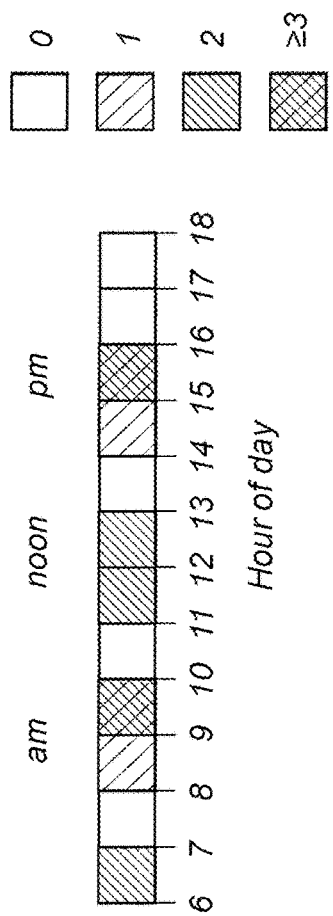
FIG. 7 is an alternative example of excrement data monitored according to an exemplary embodiment of the method of the present disclosure.
Figure 8:
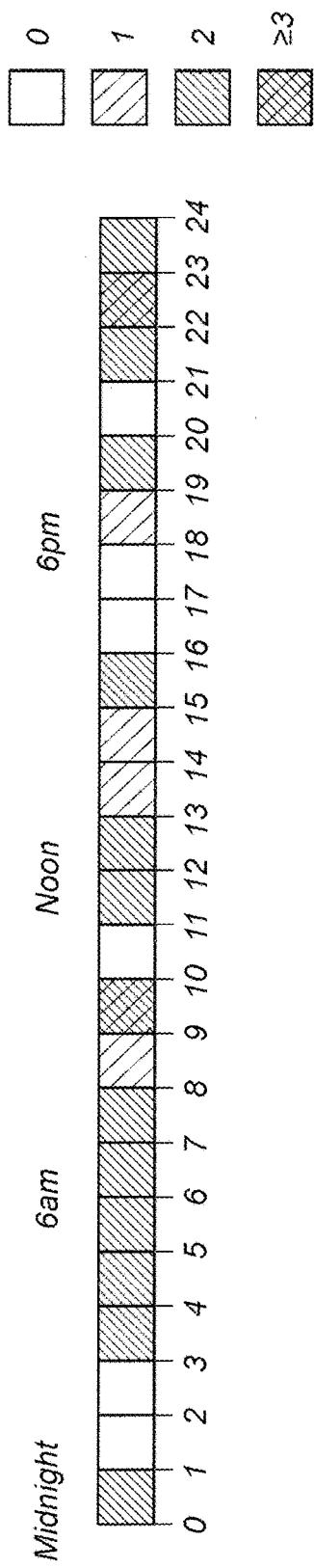
FIG. 8 is an alternative example of excrement data monitored according to an exemplary embodiment of the method of the present disclosure.
Figure 9:
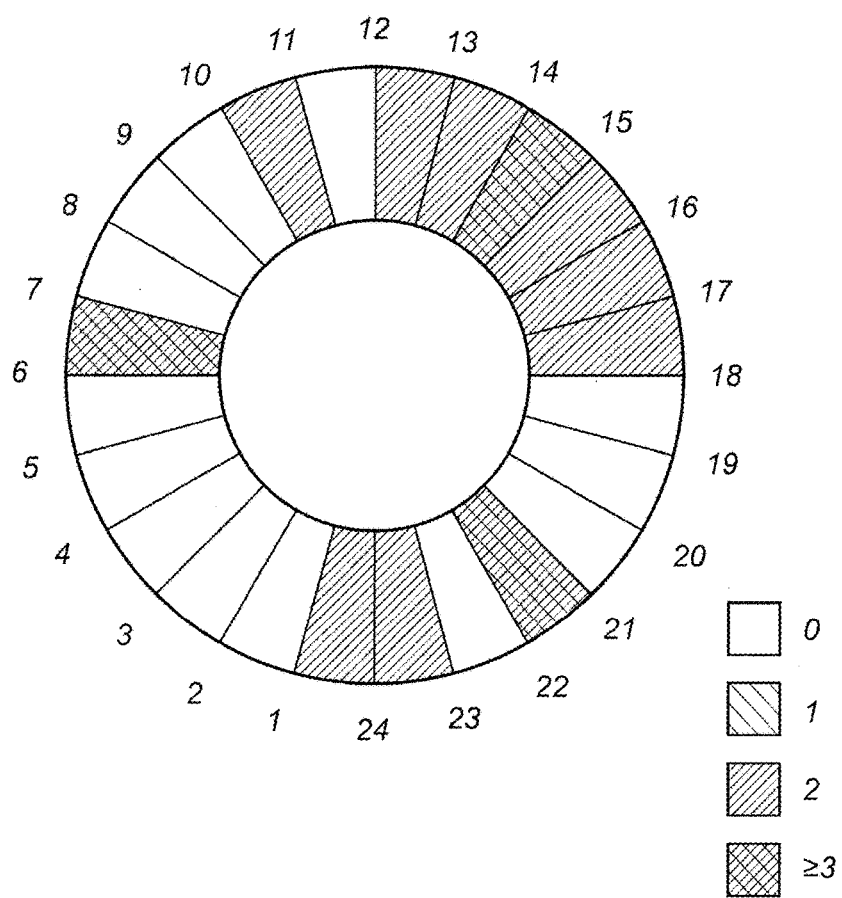
FIG. 9 is an alternative example of excrement data monitored according to an exemplary embodiment of the method of the present disclosure.

In the embodiments in FIGS. 7-9, the time intervals have equal lengths and are non-selectable by the user or care giver. That is, a person using the system, i.e. an operator or nurse, cannot select the length of the time intervals. Alternatively, the time intervals may be preselected or selected by the system. Still alternatively, the series of time intervals are determined by the method or the system adapted to perform the method.

In the embodiments in FIGS. 7-9, a sum of the length of said time intervals is shorter than the period of time corresponding to the period for which data is provided. Also, the sum of the length of said time intervals equals the length of the monitoring period.

The length of each of the predetermined time intervals is 20-150 minutes, 30-90 minutes, 45-75 minutes, or 55-65 minutes. In the embodiments in FIGS. 7-9, the time intervals have a length of 1 hour or 60 minutes.

Further, the measurement period, including all time periods for which excrement data is provided and each of which corresponds to the monitoring period, is predetermined, and has a length of two to seven times the monitoring period, a length of the measurement period is at least three times the monitoring period, or a length of the measurement period is substantially three times the monitoring period.

According to the embodiments in FIGS. 7-9, the number of associated excrement events for each time interval is associated with a graphical scheme applied to the segments of the diagram or time diagram. The graphical scheme may for instance be in form of rectangles having different heights or widths, wherein a wider or higher rectangle is associated with a higher number of excrement events. Other alternatives are a predetermined colour or shade scheme, or a colour or shade gradient, wherein a lighter colour or shade is associated with a lower number and a darker colour or shade with a higher number, or any other suitable graphical scheme, which makes the pattern easy to perceive. A colour or shade scheme may be in form of a colour or shade gradient or different density for one colour or shade, or different colours or shades for different number of events, etc.

As may be seen from FIGS. 7-9, the colour scheme of the exemplary embodiments are in form of a colour or shade gradient, wherein an increasing darkness is associated with an increasing number of associated excrement events.

In the exemplary embodiment in FIG. 7, the number of associated excrement events for aggregated or superposed data for each time interval is arranged in form of a linear time diagram extending over the monitoring period. The monitoring period of the data presented in FIG. 7 extends over a part of a day, from 06 to 18 if a 24-hour clock is used, which corresponds to 6 a.m. to 6 p.m. Each segment of the linear time diagram is associated with each of the provided time intervals. In the embodiment in FIG. 7, the length of each time interval is 1 hour and the intervals extends between 06 and 07, 07 and 08, etc. The number of excrement events associated with each interval is associated with corresponding associated segment. The graphical scheme is in form of a colour or shade gradient, such that the colour or shade saturation of the segments of the diagram associated with the intervals is proportional to the number of associated excrement events. That is, intervals with a low number of associated excrement events has a lower colour or shade saturation or a lighter colour or shade, and intervals with a high number of associated excrement events has a higher colour or shade saturation or a darker colour or shade. The excrement data includes data for a total measurement period, including the at least two different periods, covering three monitoring periods. Therefore, the colour gradient is adjusted for data covering three monitoring periods. For no events the colour or shade is white or none. For one event the colour or shade has lowest saturation or is lightest. For three or more events the colour or shade has highest saturation, or is darkest. For two events the colour or shade has higher saturation or is darker than for one event and has lower saturation or is lighter than for three events. In FIG. 7, the number of excrement events associated with the interval between 9 and 10 is 3. The number of excrement events associated with the intervals between 6 and 7, between 11 and 12, between 12 and 13, as well as between 15 and 16 is 2. The number of excrement events associated with the intervals between 8 and 9, as well as between 14 and 15 is 1. The number of excrement events associated with the intervals between 7 and 8, between 10 and 11, between 13 and 14, between 16 and 17, as well as between 17 and 18 is 0.

FIG. 8 shows another exemplary embodiment of a linear time diagram extending from 00 a.m. to 24 p.m. In other aspects, the exemplary embodiment in FIG. 8 is similar to the exemplary embodiment in FIG. 7.

In the exemplary embodiment in FIG. 9, the number of associated excrement events for each time interval is arranged in form of a circular diagram or time diagram. The circular time diagram extends over the monitoring period, wherein each segment of the circular time diagram corresponds to each of the first time intervals. The start time and end time of the circular diagram coincide. In FIG. 9, the circular diagram is in form of a 24 hour clock diagram or clock chart. Alternatively, the circumferential diagram, or time diagram, may have any other suitable form, such as quadratic, elliptic, etc. That is, the time diagram may be for instance quadratic or elliptic 24 hour clock or clock chart, or the diagram may be any other time diagram having a circumferential form suitable for illustrating the information.

Each segment of the circular time diagram corresponds to 55 to 65 minutes, especially in the example illustrated FIG. 9, each segment corresponds to 1 hour. The number of associated excrement events for each time interval is associated with a graphical scheme which is applied to the segments of said time diagram. The graphical scheme is in form of a colour or shade gradient, associating an increasing darkness with an increasing number of associated excrement events. Generally, zero excrement events associated with a time interval is associated with white colour, or no colour, or no shade. Number of excrement events associated with a time interval being equal to or exceeding number of time periods corresponding to the monitoring period for which data is provided is associated with darkest colour or shade or highest colour or shade saturation. The number of excrement events associated with a time interval being equal to between one and one half of the number of time periods corresponding to the monitoring period for which data is provided has a slightly, but clearly visibly, higher colour or shade saturation, or a slightly darker or shade colour, than white or no colour or no shade. The number of excrement events associated with a time interval being equal to between one half of the number of time periods corresponding to the monitoring period for which data is provided and less than the number of time periods corresponding to the monitoring period for which data is provided is associated with a slightly, but clearly visibly, lower colour or shade saturation or a slightly lighter colour or shade than the darkest colour or shade.

In the embodiment in FIG. 9, this corresponds roughly to that the colour or shade applied to a segment associated with an interval associated with zero excrement events is white or none. The colour or shade applied to a segment associated with an interval associated with one excrement event has lowest colour saturation or is lightest besides white. The colour or shade applied to a segment associated with an interval associated with two excrement events has a slightly, but clearly visibly, higher colour or shade saturation or is slightly darker than the lightest colour or shade associated with one excrement event. And finally, the colour or shade applied to a segment associated with an interval associated with three or more excrement events has highest colour or shade saturation or is darkest. All of the colours or shades are naturally clearly distinguishable from each other without any additional vision aids in addition to those possibly normally used by the user using the invention.

According to an alternative embodiment, not shown in the figures, the diagram or time diagram may be in form of a histogram, wherein the size, that is, either width or height, of each rectangle is proportional against the number of events per time interval. Alternatively, instead of being in form of a colour or shade gradient or different density or saturations of one colour, the graphical scheme may be in from of different colours, or shades, for different number of events, or in from of symbols having different sizes, wherein an increasing size is indicative of a higher number of events, etc.

Further, the method includes a visually representing the time diagram using suitable display means for visualising a pattern of events based on the provided data. The display means may be any suitable means such as a display, a handheld device, paper etc.

The disclosure relates also to a method for recommending toileting of a person associated with at least one absorbent article based on excrement data including an embodiment of the inventive method for analysing data and a recommending toileting an interval prior to an interval for which the number of associated excrement events are equal to or larger than the number of time periods corresponding to the monitoring period for which data is provided.

FIG. 11 illustrates a system 101 for analysing an excrement data. The system 101 includes an absorbent article and a data processing unit 17, arranged separate from the absorbent article 1. In FIG. 11, the absorbent article is shown in form of an adult incontinence product, i.e. a diaper 1. The principles of the present invention are, however, applicable to other absorbent articles such as baby or toddler diapers, sanitary towels or other known absorbent articles. The diaper 1, which is illustrated in FIG. 11, is an example of a conventional diaper except for the presence of a sensor 5 adapted to acquire excrement data. Further, the absorbent article 1 includes a control unit contact area 13 to which a control unit 18 is to be connected in order to activate each of the detection zones 9 to get an excrement reading. The contact area 13 is located at a laterally central front waist region of the absorbent article 1. The contact area 13 includes a plurality of electrical contacts 14 for making electrical contact with corresponding contacts on the control unit 18. Each conductive path 10 is connected to a respective electrical contact 14 by way of a respective electrically conductive lead. The combination of a given contact 14 and a conductive path 10 may be formed of a unitary structure (such as a conductive thread).

Figure 10:
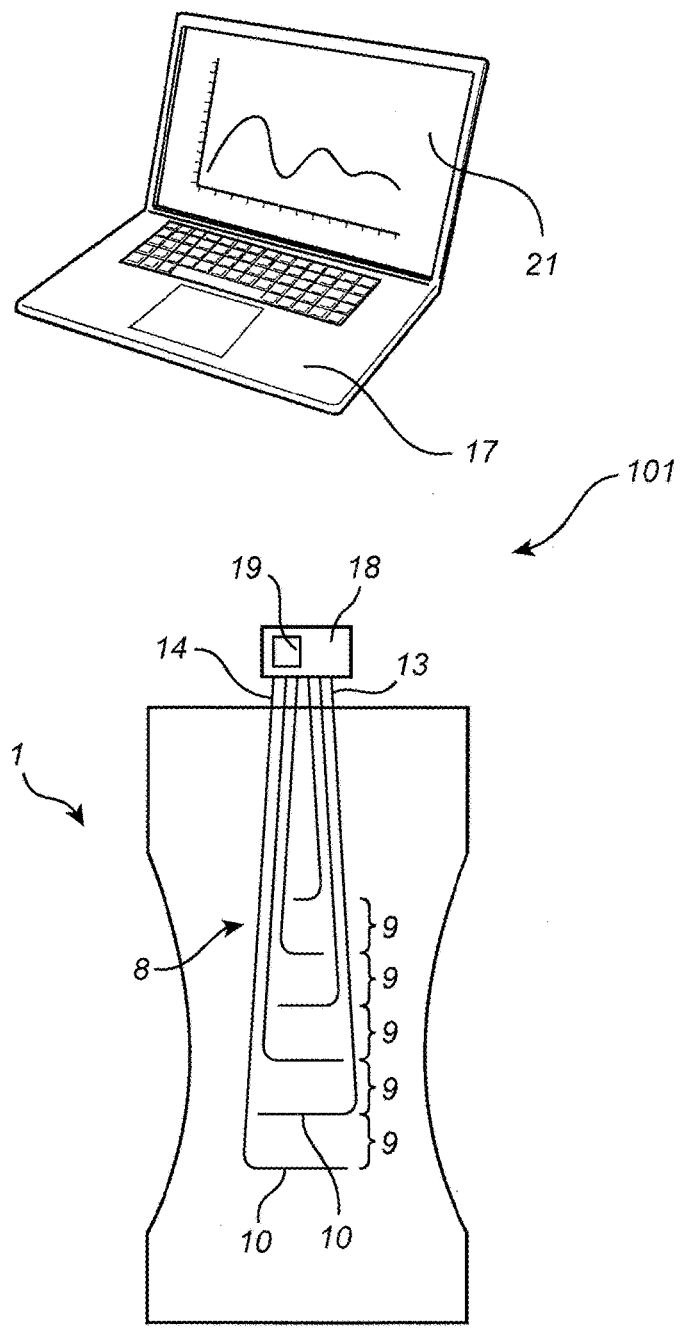
FIG. 10 illustrates a system for evaluating excrement data according to at least a first exemplary embodiment of the third aspect of the present disclosure.

Further, the exemplary embodiment of the system 101 in FIG. 10 includes a control unit 18. The control unit 18 includes contacts to engage with the contacts 14 of the protruding tab of tape of the absorbent article 1. The control unit 18 includes a memory card to provide hard memory, a memory buffer, a measurement circuit for measuring an electrical property, a clock, a battery, a wireless transmitter, and a processor 19. The battery is used to power operation of all of the components of the control unit 18.

The measurement circuit is configured to regularly apply a potential between adjacent pairs of conductive paths 10 of the absorbent article 1 and measure or indicate the impedance there between.

The processor 19 of the control unit 18 may be configured to take the measurement data from the measurement circuit and store it in the buffer until a sequence of a set of measurement data for all of the pairs is stored in the buffer. The processor is further configured to store a clock reading with each set measurement data. The storage of this set of data is repeated regularly (e.g. every second). The processor is to transfer the data from the buffer memory to a remote memory unit, such as a hard memory of some kind of central computer, for remotely recording data. Alternatively, the data may be written into a memory card, which is removable so that the stored data may be accessed by remotely located analysis software. Still alternatively, the stored data may be accessed by a cable, a USC connection or the like. In such instances, other implementations of the hard memory than a memory card may be used.

The data processing unit 17 located in some kind of central computer includes a microcomputer and software for performing at least a portion of the method according to embodiments of the invention. The data processing unit 17 is used to process the stored excrement data into a useful form for performing detecting and for evaluating excrement data according to the method described above.

A receiver arranged in the central computer is used to retrieve the data transmitted by the transmitter of the control unit 18. Thereafter the excrement data is inputted into the data processing unit 17. The data processing unit 17 may take the excrement data for each of the detection zones 9 from the memory and detect excrement events. Alternatively, the data processing unit 17 is configured to receive sets of data indicating excrement events into the absorbent article. Further, the data processing unit 17 is adapted to perform or execute an embodiment of the inventive method for analysing excrement data described above. That is, the processing unit provides a series of time intervals; and associates or correlates the time mark of each excrement event with a corresponding time interval. Further, data processing unit is further configured to estimate a pattern of excrement events based on the association/correlation of the time mark of each excrement event with a corresponding time interval. The data processing unit 17 includes means for estimating a toileting schedule for a person associated with said absorbent article 1, based on said estimated pattern of excrement events.

Instead of being integrated in a central computer, the data processing unit 17 may be integrated in a cell phone, some kind of handheld computer, etc. Still alternatively, instead of including both a processing unit 19 integrated in the control unit 18 and a remote data processing unit 17 integrated in the central computer, the system may include the single data processing unit 17, 19 integrated into the control unit 18 alone or in the computer 2 alone. In such a case, the single data processing unit 17, 19 of the control unit 18 or computer 2 is adapted to acquire data as well as to process it.

Further, the exemplary embodiment in FIG. 10 includes a display unit 21, which is an example of output means for visually representing the number of associated or correlated time marks of each excrement event for each corresponding time interval for visualising a pattern of excrement events based on the provided excrement data. The display unit 21 is connected or connectable to the data processing unit 17 and arranged to display the result of embodiments of the inventive method, such as the excrement data analysed such as a pattern of excrement events is apparent as well as a visual representation of the number of excrement events associated with each interval.

The diaper 1, which is illustrated in FIG. 10, is an example of a conventional diaper except for the presence of a wetness or liquid discharge sensor 8, which is an example of a sensor, including a plurality of wetness detection zones 9 (in this specific example, there are five wetness detection zones 9). The wetness sensor 8 is adapted to generate an electrical output signal representative of a wetness state or degree of wetness of the absorbent core of the diaper 1. The wetness sensor 8 includes several zones or segments 9 and is responsive to a change in an electrical property in the core of the absorbent article and includes conductive material arranged in contact with the core of the absorbent article. The electrical property is conductance, resistance, or other electrical properties linked to these. In the exemplary diaper 1 in FIG. 6, each detection zone 9 includes first and second electrically conductive paths 10 (in the form of electrically conductive threads, or other electrically conductive material) that are longitudinally spaced from one another along a longitudinal axis of the absorbent article 1. The conductive paths 10 are in physical and electrical contact with the absorbent core. The end detection zones 9 share a conductive path 10 with an adjacent zone, while the middle detection zones 9 share both conductive paths 10 with their adjacent detection zones 9.

The sensor is a disposable sensor and intended to be used once and disposed together with the used absorbent article. Further, the sensor is arranged inaccessibly for a user in the absorbent article and is integrated into the absorbent article.

That is, the sensor is not accessible to the user without at least partly breaking the absorbent article.

The scope of the invention according to the claims is not limited to the diaper 1 described above or the wetness sensor 8 described above. The principles of the present invention are, however, applicable to other absorbent articles such as baby or toddler diapers, sanitary towels or other known absorbent articles. Further, the principles of the present invention are applicable to other suitable sensors 8 including one detection zone 9 or a plurality of detection zones 9 as well. Alternatively, the sensor may be any other suitable sensor which is responsive to an excrement event in the absorbent article, such as another wetness or liquid discharge sensor responsive to a change in an electrical property in the absorbent article, including conductive material, a temperature sensor, a gas sensor etc. Still alternatively, the sensor may be reusable and adapted to be attached to and detached from the absorbent article.

It is also useful to determine the length of time, particularly in a system of absorbent articles, before a first excrement event. The data begins at time zero when the control unit is first contacted with the contacts of the absorbent article. The system is thus configured to determine the length of time from when data is first recorded for that absorbent article to when the impedance measurement shows that a first excrement event has occurred. Further, the time between the first excrement and any subsequent excrement events is recorded. The time data is stored in the excrement data and the data processing unit is configured to evaluate the data.

The disclosure also relates to a system for recommending toileting based on excrement data including the system for evaluating data and means for recommending toileting an interval prior to an interval for which the number of associated excrement events are equal to or larger than the number of monitoring periods for which data is provided.

Even though the invention has been described with reference to specific exemplifying embodiments thereof, many different alterations, modifications and the like will become apparent for those skilled in the art. For example, additionally, variations to the disclosed embodiments may be understood and effected by the skilled addressee in practicing the claimed invention, from a study of the drawings, the disclosure, and the appended claims. In the claims, the word "comprising" does not exclude other elements or steps, and the indefinite article "a" or "an" does not exclude a plurality. A single unit may fulfil the functions of several items recited in the claims. The mere fact that certain measures are recited in mutually different dependent claims does not indicate that a combination of these measured cannot be used to advantage.

The invention claimed is:

1. A method for monitoring excrement data for seeking a pattern for a monitoring period, wherein said excrement data is associated with at least one absorbent article and a person wearing said at least one absorbent article, the method comprising:
    acquiring excrement data, from a sensor associated with an absorbent article, comprising excrement data for at least two different time periods, wherein each of the at least two different time periods corresponds to the monitoring period for which a pattern of events is sought, wherein said excrement data comprises information of excrement into an absorbent article in form of excrement events, and wherein each excrement event has an associated time mark or associated information from which an associated time mark may be derived;
    smoothing the time mark of each excrement event;
    superposing the excrement data of the at least two different time periods such that the number of excrement events for each of the at least two different time periods is distinguishable and hours of each of the at least two different time periods coincide with hours of the monitoring period;
    identifying peaks of the superposed data and estimating a time mark corresponding to the identified peaks; and
    initiating toileting by the person during a time interval prior to the estimated time marks corresponding to the identified peaks.

2. The method according to claim 1, wherein said excrement data is in form of absorbent state data and an excrement event is indicated by a change of the absorbent state of the absorbent article.

3. The method according to claim 1, wherein said excrement data is in form of electrical property data and an excrement event is indicated by a change of the electrical property of the absorbent article.

4. The method according to claim 1, wherein the smoothing comprises smoothing by applying a Kernel smoothing method.

5. The method according to claim 4, wherein the Kernel smoothing method comprises applying a Kernel function to the time mark of each excrement event.

6. The method according to claim 5, wherein a bandwidth, h, of said Kernel function is 20-150 minutes.

7. The method according to claim 1, wherein identifying peaks of the superposed data includes identification of each peak having a height $\geq 0.8\ n*k$, wherein n is number of different periods for which data is acquired corresponding to the monitoring period and k is the height of the smoothing function.

8. The method according to claim 7, wherein the smoothing comprises smoothing by applying a Kernel function to the time mark of each excrement event, and wherein a bandwidth, h, of said Kernel function is 20-150 minutes.

9. The method according to claim 8, wherein said time interval has a length corresponding to the bandwidth.

10. The method according to claim 1, wherein the total number of periods of time for which data is acquired corresponding to the monitoring period is pre-determined.

11. The method according to claim 1, further comprising plotting the resulting superposed data as a continuous curve over the monitoring period for visualising a pattern of excrement events based on the acquired data.

12. The method according to claim 1, wherein the number of associated excrement events for each time interval is arranged in form of a circumferential diagram extending over the monitoring period, wherein each segment of the diagram corresponds to each of the time intervals.

13. The method according to claim 1, wherein the number of associated excrement events for each time interval is associated with a graphical scheme which is applied to segments of a circumferential diagram.

14. The method according to claim 13, wherein the graphical scheme is in form of a colour gradient.

15. A data processing unit for monitoring excrement data is adapted to:
    acquire excrement data, from an absorbent article with a wetness or liquid discharge sensor, comprising excrement data for at least two different time periods, wherein each of the at least two different time periods corresponds to a monitoring period for which a pattern of events is sought, wherein said excrement data comprises information of excrement into an absorbent article in form of excrement events, and wherein each excrement event has associated information from which an associated time mark may be derived;

smooth the time mark of each excrement event;

superposing the excrement data of the at least two different time periods such that the number of excrement events for each of the at least two different time periods is distinguishable and hours of each of the at least two different time periods coincide with hours of the monitoring period;

identifying peaks of the superposed data and estimating a time mark corresponding to the identified peaks; and providing instructions for initiating toileting by the person during a time interval prior to the estimated time marks corresponding to the identified peaks.

16. A data processing unit for monitoring excrement data adapted to perform the method according to claim 1.

17. A system for monitoring excrement data, comprising:

an absorbent article comprising a wetness or liquid discharge sensor, which is arranged to generate an output signal representative of an excrement status of said absorbent article, and a data processing unit adapted to process said output signal generated by the wetness or liquid discharge sensor, wherein said data processing unit is adapted to:

acquire excrement data, from said wetness or liquid discharge sensor, comprising excrement data for at least two different time periods, wherein each of the at least two different time periods corresponds to a monitoring period for which a pattern of events is sought, wherein said excrement data comprises information of excrement into an absorbent article in form of excrement events, and wherein each excrement event has associated information from which an associated time mark may be derived;

smooth the time mark of each excrement event;

superposing the excrement data of the at least two different time periods such that the number of excrement events for each of the at least two different time periods is distinguishable and hours of each of the at least two different time periods coincide with hours of the monitoring period;

identifying peaks of the superposed data and estimating a time mark corresponding to the identified peaks; and providing instructions for initiating toileting by the person during a time interval prior to the estimated time marks corresponding to the identified peaks.

18. The system for monitoring excrement data according to claim 17, further comprising output means for visually representing the superposed excrement data for visualising a pattern of excrement events for the person associated with the absorbent article, based on the acquired excrement data.

* * * * *